Figure 2:
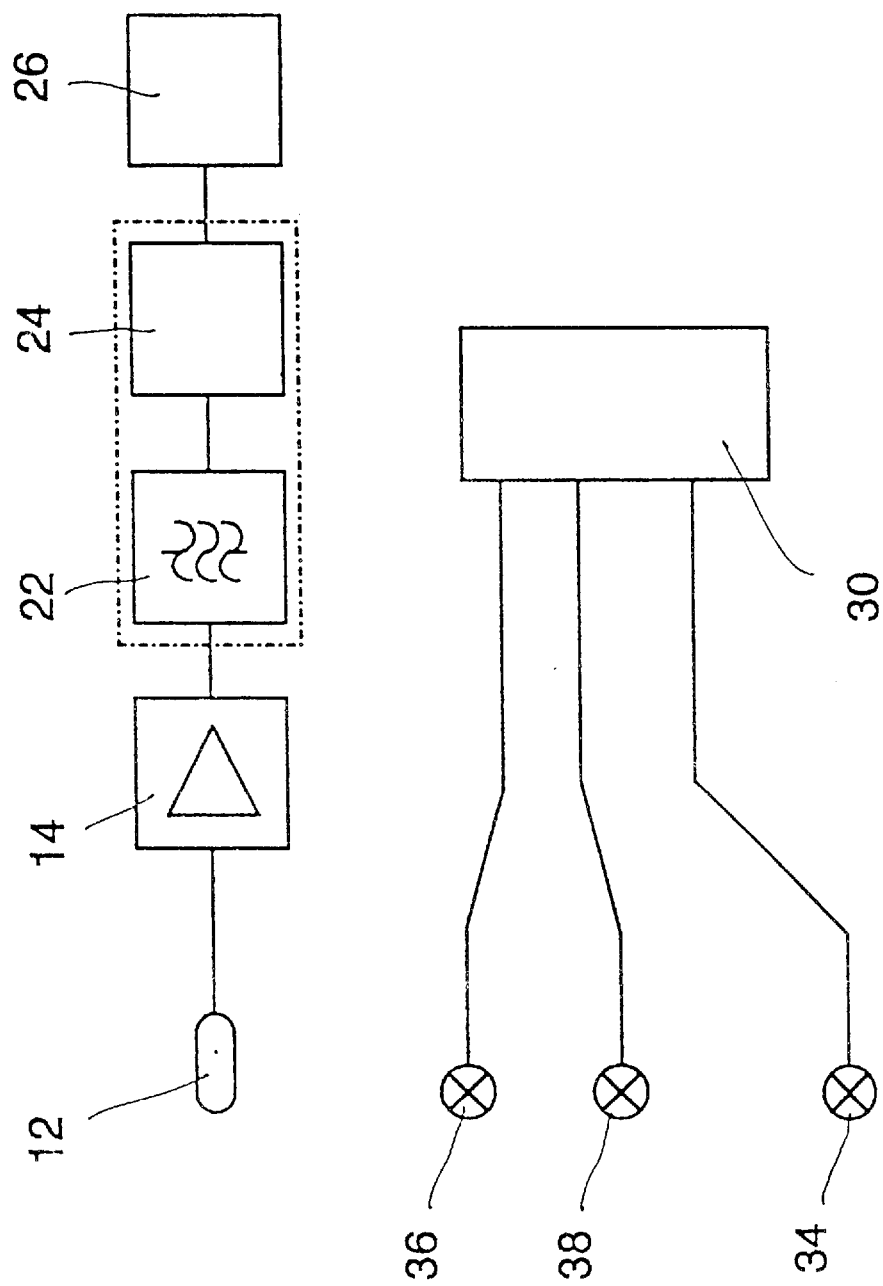

United States Patent [19]
Voipio

[11] Patent Number: 5,823,190
[45] Date of Patent: Oct. 20, 1998

[54] AUTOMATIZATION OF ELECTRO-OCULOGRAPHIC EXAMINATION

[76] Inventor: Ville Sakari Voipio, Riihitie 15 A 4, FIN-00330 Helsinki, Finland

[21] Appl. No.: 586,642
[22] PCT Filed: May 13, 1994
[86] PCT No.: PCT/FI94/00191
　　§ 371 Date: Jul. 8, 1996
　　§ 102(e) Date: Jul. 8, 1996
[87] PCT Pub. No.: WO94/26165
　　PCT Pub. Date: Nov. 24, 1994

[30] Foreign Application Priority Data

May 14, 1993 [FI] Finland ................................. 932222

[51] Int. Cl.⁶ .......................................... A61B 5/04
[52] U.S. Cl. ........................... 128/745; 128/733; 128/639
[58] Field of Search ................................. 128/745, 733, 128/639

[56] References Cited

U.S. PATENT DOCUMENTS

| | | |
|---|---|---|
| 4,474,186 | 10/1984 | Ledley et al. . |
| 4,561,448 | 12/1985 | Buchas . |
| 4,595,017 | 6/1986 | Semenov et al. . |
| 4,653,001 | 3/1987 | Semenov et al. . |

FOREIGN PATENT DOCUMENTS

| | | |
|---|---|---|
| 3511695 | 10/1985 | Germany . |
| 3511697 | 9/1988 | Germany . |
| 2157000 | 10/1985 | United Kingdom . |

*Primary Examiner*—Vincent Millin
*Assistant Examiner*—Robert N. Wieland
*Attorney, Agent, or Firm*—Browdy and Neimark

[57] ABSTRACT

The invention is especially related to a method for performing an electro-oculographic (EOG) examination of the eyes. Alternating optical signals are produced (34, 36) for the stimulation of the eye movement and those changes in the bioelectric potentials are observed (12), which changes are caused by the eye movements corresponding to said optical signals, for the establishment of sample signals. Noise signals are filtered (22) off by forming a moving average from successive sample signal portions, defining from said average signals the potential leaps or transitions in the biopotential signals, which transitions are caused by said eye movements, and calculating (24) values corresponding to said transitions. Possible distorted values are removed from the set of said values and finally the EOG ratio is defined on the basis of values selected from the remaining set of values.

More generally the invention relates to a method for determining, from a sample signal comprising potential leaps and spurious noise, a reference value for a potential leap. From the analogue sample signal a digital signal succession is formed from the successive signal portions of which moving averages are calculated. An approximate potential leap point is obtained from said average signals by windowing at an area where a transition is supposed to exist.

The invention further relates to an apparatus for the realization of an EOG examination in accordance with a method disclosed above.

11 Claims, 5 Drawing Sheets

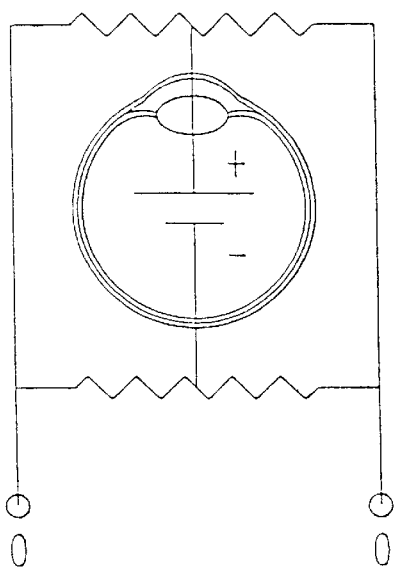
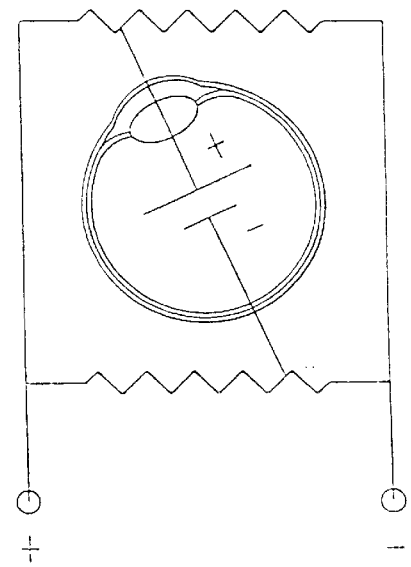
Fig 1a Fig 1b
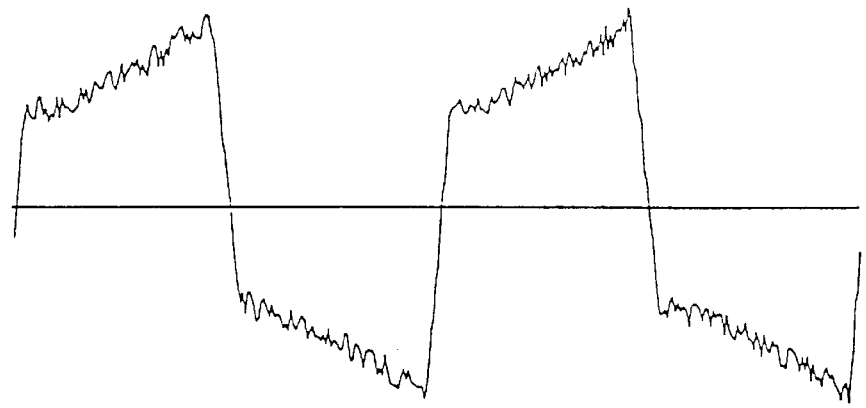
Fig 4a
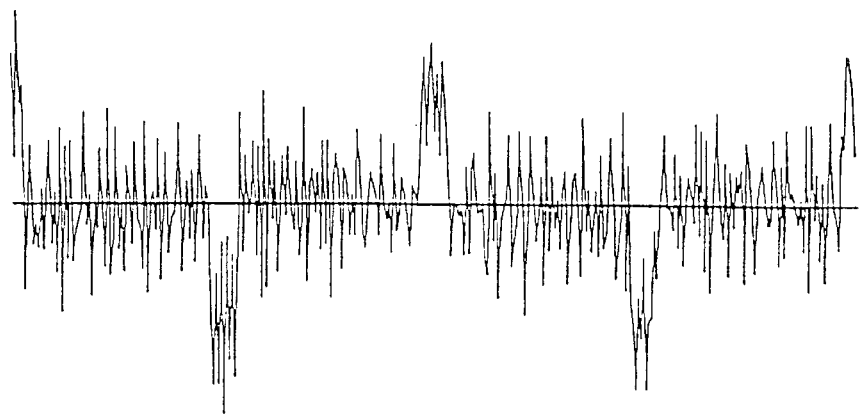
Fig 4b $l = 5$ $l = 10$ $l = 20$ $l = 40$

AUTOMATIZATION OF ELECTRO-OCULOGRAPHIC EXAMINATION

The present invention relates to a method as defined in the introductory part of claim 1, as well as to an apparatus for the realization of said method for carrying out an electro-oculographic (EOG) examination, said method being used for detecting certain types of damages in the retina. Especially the invention relates to a method for speeding up and facilitating to the EOG examination by automatizing it. More generally the invention is directed to a method for determining a reference value for a potential leap from a sample signal comprising potential leaps and spurious noise.

The invention further is related to an apparatus as defined in the introductory part of claim 7, for the realization of the method according to the invention.

Electro-oculography is an electro-physiological examination centrally related to opthalmology, said examination being based on the measurement of slow fluctuations in the electrical potential differences between the retina (– pole) and the cornea (+ pole). The ratio between said cornea-retinal potentials is called the EOG-ratio. EOG is used for the examination of certain degeneration diseases in the retina. It may further be used for ascertaining whether a medication used e.g. for curing rheumatism is damaging the retina. Thus, EOG examination is considered to be essential in patient examination, but it is also considered to be a good examination method in experimental studies and especially when carrying out retina toxic examinations for medicines.

The potential cannot be directly measured at the eye. This could be done by arranging an electrode on the cornea, but in this case the eye must be anesthetized, which would lead to erroneous results due to the abnormal function of the eye.

This problem is avoided by measuring the EOG ratio indirectly using electrodes arranged in the vicinity of the patient's eyes, whereby mutually different biopotentials, which can be measured, are formed by the movement of the eyes. The biopotential ratio for an eye can then be defined by calculation from the mutual ratio of said bio potentials. Depending on the test arrangement a varying amount of electrodes are arranged on the skin, and further there are numerous different positioning alternatives for them. The movement of the eyes is accomplished using e.g. blinking light sources. In a widely used test arrangement the patient looks at two light sources arranged at opposite sides of his eyes. The lights blink in opposite phases at a frequency of e.g. 1 Hz, so that the patient's eyes are in a constant movement back and forth. Also such a test arrangement is known where a fixed light or some other distinct target is moved in front of the patient's eyes.

The potential always varies when the patient moves his eyes. The wave frequency of the potential amplitudes thus initiated is identical with the blinking frequency of the light source.

The size of the potential amplitude is proportional to the EOG ratio, since the potential is zero when the eye looks straight ahead and correspondingly differs from zero when the eye looks sideways or upwards.

Since the potential depends on the position of the eye and on the cornea-retinal potential it is impossible to define the real cornea-retinal potential. This fact, however, is unsignificant, since the potential ratio achieved as a result of the examination is more important. It is, however, important that during the examination the eye moves between the same suitably defined points.

The examination itself is usually started in darkness. The potential difference signal is recorded for about 10 seconds once in every minute during a fifteen minute period. The signal is not measured continuously, because the continuous moving of the eyes is very exhausting, which would distort the results. Also, the changes in this type of cornea-retinal potential are very slow.

First the cornea-retinal potential decreases slowly when the eye adapts to the darkness. This should happen in about 8 to 9 minutes from the beginning of the examination. After this dark fifteen-minute period the light is changed to a very bright one. Then another fifteen-minute period is recorded. The cornea-retinal potential should rise as the eye adapts to the new lighting. This takes again about 8 to 9 minutes.

After this the EOG ratio is defined taking the highest and lowest cornea-retinal potential values and calculating their ratio. If this ratio is below a defined limit the case usually needs closer investigations.

However, manually performing this kind of examination has been a very tedious task. Different apparatus, like the light source, the measuring equipment and the plotter, must be started and stopped a number of times. One must know how to select the "good" samples from among the ones obtained, and their average values must be calculated, after which a graphic presentation is made for the average values of each examination period, from which presentation the EOG ratio finally can be defined. It is usual to obtain about 1000 "good" potential amplitudes to be defined manually, which increases the calculation error possibility at the average value calculation. In the examination it is further possible to include several special functions which also demand much attention from the examiner.

For said reasons an automatic performance of the examination sequence has been suggested, e.g. controlled by a processor or logical circuit. In U.S. Pat. No. 4,474,186 there is suggested an apparatus which automatically controls an electro-oculographic examination and automatically processes the results derived from the examination and presents these results in a readable form. The arrangement thus developed is, however, rather complicated and the results obtained therefrom have not proven to be exact enough. Especially the weakness of the amplitudes obtained from the electrodes has caused unexactness, since the relevant signals tend to be covered by random electromagnetic and biological background noise, said noise distorting the signal obtained and essentially complicating the achievement of reliable results. The ability of the electronic error filter system in the apparatus according to the cited document to separate "good" and "poor" samples from each other has also proven insufficient, since it is based on a low and high pass filtering of the noise signals. However, the electrodes provides such a weak signal that it is especially difficult to select filters capable of providing a sufficient amount of reliable results after filtering which still not simultaneously filtering away a considerable portion of the signal. Especially due to the high error probability in the results given by the apparatus according to the cited publication no significant improvement in the EOG examination has actually been achieved therewith.

Further, in the publications DE 3511695 and DE 3511697 complicated systems for the automatization of EOG examinations are disclosed. In these known systems the filtering of the signals and the poor reliability of the results also constitute a problem, since both the systems according to said cited publications use low and high pass filtering for the noise reduction.

Further, all the known systems discussed above have been confronted with the fact that the computer's pattern recognition ability is insufficient. The computer has not been able to define exact enough EOG values from the signal graph obtained, and especially the insufficient pattern recognition ability has increased the asymmetry and non-continuousness in the graphs.

The object of the present invention is to overcome the disadvantages in the prior art and provide a quite new solution for performing an automatic EOG examination exactly and quickly, in a reliable and even very simple manner.

Another object of the invention is to provide a functionally simple and easy-to-use method and apparatus for the performance of an EOG examination.

Yet another object of the invention is to provide an apparatus and method which give the results of an EOG examination in real-time.

Yet another object of the invention is to provide such an apparatus for the automatic performing of an EOG examination, which apparatus may be realized using easily accessible standard components and a micro processor.

The invention is based on the idea that the signal obtained from the electrodes is subjected to a computer aided median filtering, i.e. a moving average value is defined from the signal's subsets, the signal favorably being digitized prior to the median filtering. The filtered signal is derivated and, using the peak of the derivative signal and a second point defined in accordance with the teaching of the present invention, the real level of the potential leap is defined by integration. Using the method according to the present invention the system's ability to differentiate between "good" and "poor" signals will be essentially improved.

In this connection it should be observed that the digitalized signal is not continuous but represents the peak value for samples taken per time unit. In a purely mathematical observation such a non-continuous signal cannot have any derivative. Since, however, the difference between two adjacent samples will behave- like a derivative it will, in this connection, be called a derivative, which can be expressed as:

$$dx_n = x_n - x_{n-1},$$

where n is an integer

In this connection the term integral is used to express the corresponding relation between two adjacent samples, which behaves like an integral and can be expressed as:

$$\int_a^b x(n)dn => \sum_{n=a}^{b} x_n$$

Further, in this connection the term transition will be used to indicate a potential leap.

More exactly expressed, the method according to the invention is mainly characterized by the features disclosed in the characterizing parts of claims 1 and 6. The apparatus according to the invention is characterized by the features disclosed in the characterizing part of claim 7. Other characterizing features are found in the dependent claims.

According to a preferred embodiment of the invention an EOG examination of the eyes is performed automatically so that the examiner does not at any stage after the initiation of the examination cycle need to interfere with the examination procedure, but the system according to the invention will independently perform the action cycles of the examination, perform the removal of error signals, analyze the obtained measured results as well as store and print them in a desired form.

Reliable and exact results will be obtained using the method according to the invention, where signals obtained from electrodes arranged on the skin will be digitalized and median filtered for the elimination of erroneous signals. The signal obtained is derivated whereby an essentially symmetric triangular form is achieved for the obtained signal pattern.

In the next step the minimum and maximum of the essentially triangular derivative signal is localized. In this respect forming of a window may be used, the window being applied around that point where a maximum is believed to occur. The length of the window is preferably defined as the length of one phase of the light source flash. The centre of the window will not be exactly where it theoretically should be, since due to the reaction time a person will move his eyes with a slight lag with respect to the light source and thus also the window will be located slightly later than the light source cycle.

At the setting of the windows it should further be investigated whether a minimum or a maximum of the signal will occur first. This is done by assuming a maximum to come first and setting the windows accordingly. Thereafter the signal values are multiplied with 1 in maximum windows and with -1 in minimum windows. If the average of the values thus calculated is positive the presumption was correct and if the average value is negative the first window was located at a minimum.

Now the exact positions of the peaks are known. Next the position of the edges of the triangular peak area should be found. The remaining noise in the signal makes it impossible to define the position of the edges using the signal zero points. Further, the last edge of a peak is normally further away than the first edge.

For this procedure the form of the peak is utilized. After the median filtering the peak should have straight edges. Finding the position of the edges and the peak end is started at the maximum and the samples are searched one after the other, moving forwards away from the maximum until the average of all the samples between the present position and the maximum is half the maximum. Using this position point and the maximum point the end point of the peak is obtained for the calculation of the area.

Finally the amplitude size is simply obtained by integrating over the peak area of the curve, whereby the real amplitude height is obtained.

The calculation is preferably performed using a computer and it can preferably be made faster by combining the median filter and derivation stages.

The method according to the invention will give several remarkable advantages. Not only will the analysis of the signals obtained from the electrodes be faster with respect to prior art, but the obtained results will also be more exact and reliable. The apparatus needed for performing the examination and the method according to the invention is easy to realize and favorable regarding the costs, since all the components needed are of a type which can be commercially obtained.

Figure 3:
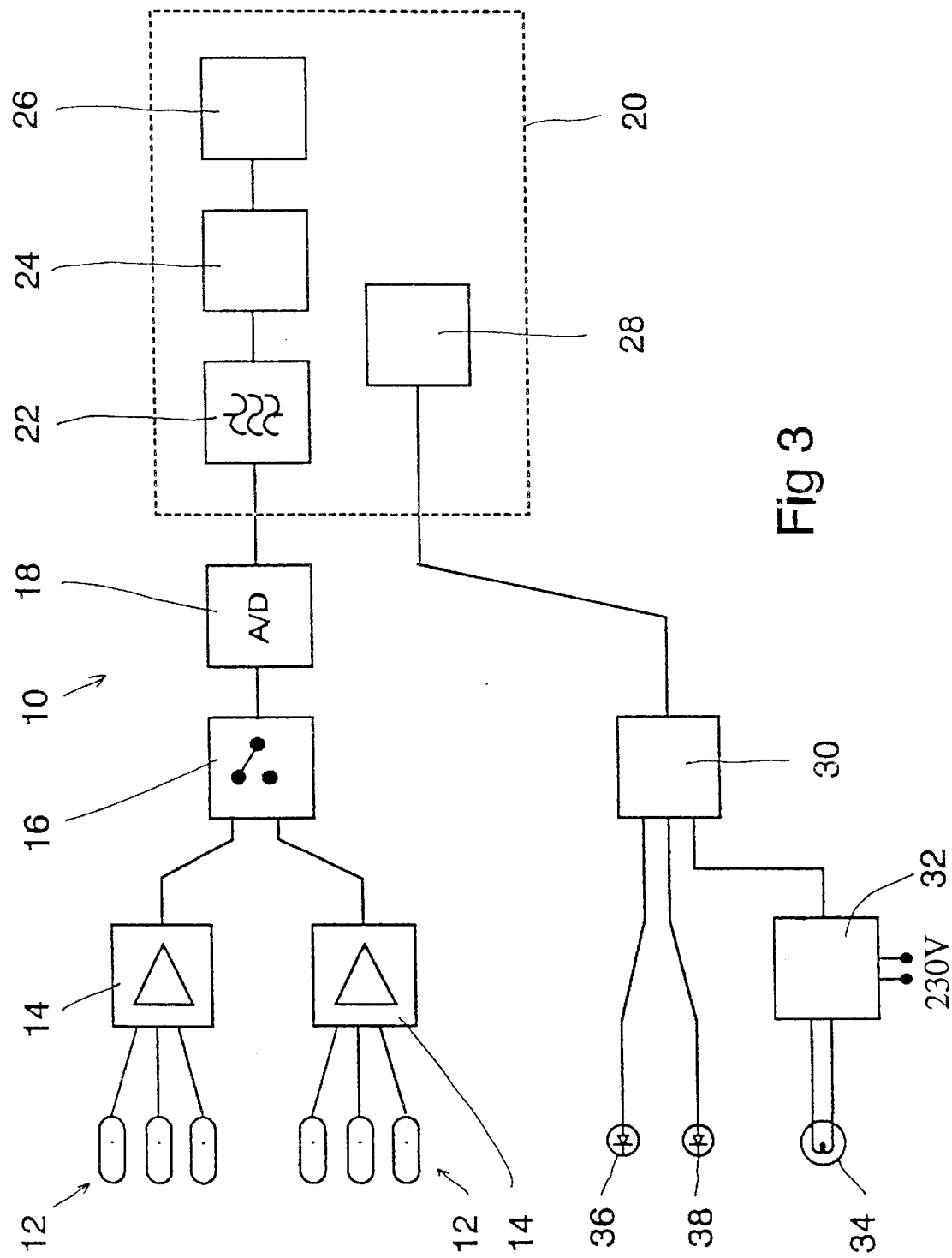
Figure 5:
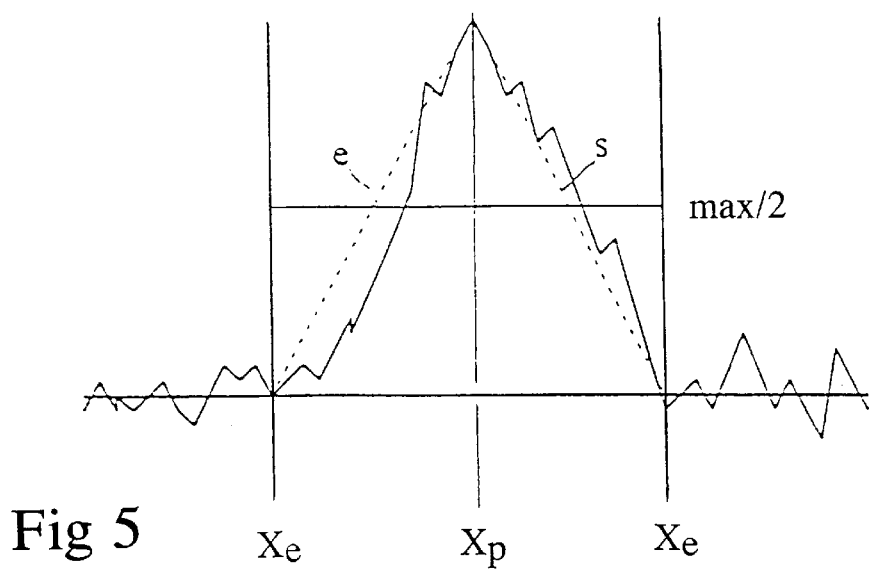
Figure 7:
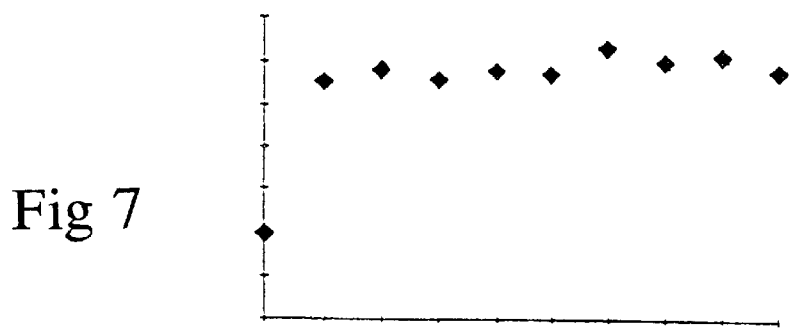
Figure 8:
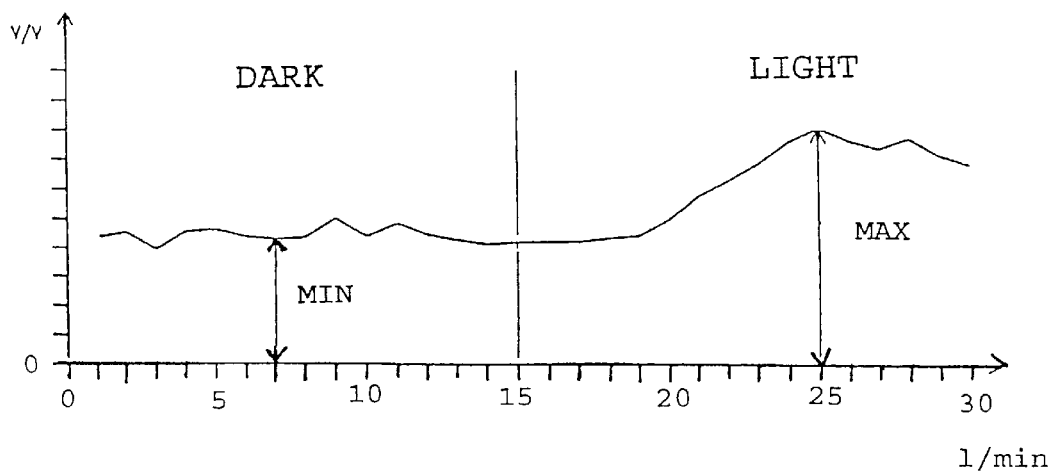
Figure 6A:
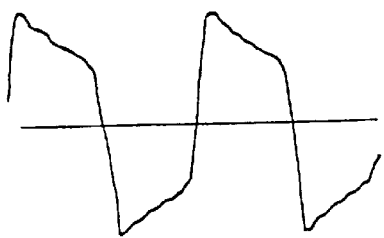
Figure 6B:
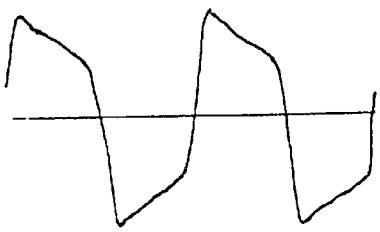
Figure 6C:
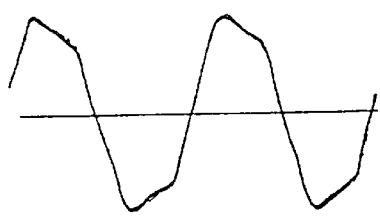
Figure 6D:
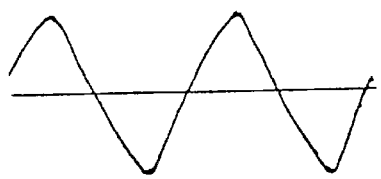
Figure 6A:
Figure 6B:
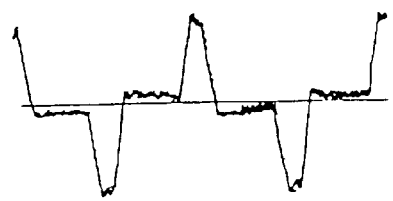
Figure 6C:
Figure 6D:
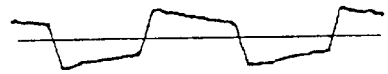

Below an embodiment of the invention will be described with reference to the accompanying drawings, where:

FIGS. 1a and 1b schematically show the electrical circuit formed by the eyes and they show the potential level when the eye looks straight ahead and to the side, FIG. 2 is a schematic disclosure of the main idea of the invention, FIG. 3 is a schematic disclosure of an apparatus according to one preferred embodiment, FIGS. 4a and 4b show a measured signal, FIG. 5 shows the same signal as derivated but without median filtering, FIGS. 6A–6D' shows measured results obtained using different filter lengths 1, in FIGS. 6A and 6A' 1=5; in FIGS. 6B and 6B' 1–19; in FIGS. 6C and 6C' 1=20; and in FIGS. 6D and 6D' 1=40, FIG. 7 shows sizes of potential leaps calculated from measured signal values, and FIG. 8 shows EOG values obtained in one examination.

More precisely, FIG. 1a discloses the electrical circuit formed by a human eye, and its potential when said eye looks straight ahead. Favorably the nose base and the temples are used as measuring points for the biopotential, i.e. as attachment points of the measuring electrodes 12, but other locations may be used too. Said electrodes 12 are connected to an amplifier 14, which can be a conventional EKG-apparatus or the like. As can be seen from the figure, the potential of the circuit is essentially zero when the eye is looking as indicated in the figure.

In FIG. 1b the eye is shown turned to the left, and it can be observed, that the temple electrode potential now is higher than that of the electrode 12 at the nose base.

During the examination procedure it is important that the eye moves between the same two points. Further a too excessive angle between light sources will cause the patient's eyes to be rapidly wearied and then the signal will loose its sharp form. On the other hand, a too narrow angle will give too low potential leap values from which it is impossible to define the EOG ratio. As a suitable angle would be about 15 from the center line to both sides of eyes, as indicated above.

FIG. 2 schematically shows the basic idea of the present invention in one of its simplest embodiments. According to the figure the signal obtained from the electrodes 12 is amplified in an EKG-amplifier 14, filtered in a median filtering means 22, which is functionally connected to said amplifier, the correct signal transition is obtained by a calculation means 24, which is functionally connected to said median filter, and said signal is favorably stored and displayed in storage and display means 26. Said median filtering means 22 and calculation means 24 may also favorably be combined, as indicated by a line of dots and dashes, whereupon they will simultaneously handle the same signal. Further, the operation of the blinking lights 36, 38 and the general lights 34 are controlled by incentive control means 30. All the sequences performed by these means, except for the amplifying phase performed by the amplifier 14, can preferably be performed programmatically using a microcomputer.

FIG. 3 schematically shows a favourable apparatus embodying the invention, said apparatus being generally indicated by the reference 10. Said apparatus comprises electrodes 12, which are functionally connected to EKG-amplifiers 14. Usually one such amplifier is needed for each eye. Said EKG-amplifiers 14 are functionally connected to a selector device 16 which preferably is connected to an A/D converter device 18. Said apparatus 10 further comprises a computer 20, which is functionally connected to said converter 18 and comprises said median filtering means 22, said transition calculator means 24 as well as said storage and display means 26. Said computer 20 further comprises said incentive control means 28, which means are functionally connected to the actual incentive controller 30. Said controller 30 controls the function of said general light 34 which is functionally connected to said blinking incentive lights 36, 38 and a relay 32.

Said amplifiers 14 must be completely isolated, i.e. none of the three electrodes may have a fixed potential. This is very important with respect to the patient security.

Another important feature is that said amplifier 14 comprises three electrodes 12. Two of said electrodes are differential electrodes, between which the potential difference is measured. The third electrode is an active zero electrode which feeds the measured signal back to the patient, which feature will decrease the measured noise level. This especially attenuates the strong 50 Hz signal.

A test arrangement set up according to FIG. 3 comprised two amplifiers, both being Kone 521 EKG amplifiers. in order to reduce the number of electrodes needed the active zero electrodes of each amplifier were interconnected. This is possible since said electrodes are completely isolated. Said test arrangement further comprised a notch filter tuned for 50 Hz.

The amplification factor for the amplifiers used is 2000. This is quite suitable because a typical potential difference in an EOG examination is about 1 mV. Thus the amplifier's output voltage is between −2V and +2V.

The interface card for the computer included in the test apparatus comprises several functions when an EOG value is measured. It stores all measured results, controls said light sources and acts as voltage supply for said EKG amplifiers.

The used computer interface card had the following properties:

a two channel A/D converter having high impedance inputs a power source (60 $V_{pp}$ 20 KHz) for the isolation transformers in the amplifier a TTL level signal output for controlling the light source and 2 outputs for controlling the LEDs a direct connection to an IBM PC or a PC/AT ISA data bus.

Since this kind of ready made cards could not be obtained said card was constructed and composed according to the above disclosed principles on an IBM card having a ready connection to the ISA data bus and an address encoding logic. For the person skilled in the art it is evident that the processing arrangement according to the invention as such can be performed in several different manners.

The next task comprises the definition of the size of the potential leaps from the EKG signal. For human beings this is not any especially difficult task, since humans have a rather developed pattern recognition ability and thus a slight noise in the measured signal does not significantly disturb the recognition process. Unfortunately, a computer cannot perform such a pattern recognition, and thus mathematical rules based on statistical methods must be deduced for this purpose.

As already is mentioned, the leaps are quite evident for a human being. Unfortunately they cannot be found at standard locations, since each patient will move his eyes at a slightly different speed. Thus, each step must be found independently.

FIG. 4b discloses the signal after derivation, which signal in FIG. 4a is disclosed without a median filtering. The derivation is performed in order to define the points where the patient moves his eyes. As evident from FIG. 4b a random noise will produce a derivative which is undulating to quite a high extent and which has very little regularity, except for a rather clear initial signal. From this curve it is difficult even for the human pattern recognition ability to find similarities with the actual signal curve. Thus, it is important to reduce the disturbing amount of noise.

In FIG. 5 one derivated signal peak is disclosed. As is evident from this figure the median filtering broadens the peak producing a clearly triangular form. The processing of said peak starts with the defining of the maximum of said peak. Here the problem is to find a local maximum $x_p$. The task is not difficult if the signal is as clear and clean as the signal shown in FIG. 5, but in practice the patient's eyes sometimes "get lost", i.e. they look somewhere else and not at the light source, and-this produces small local maxima. These error maxima are excluded from the real maxima in a manner to be disclosed hereafter.

It is known that the real peaks come in a regular order, i.e. a maximum must follow a minimum and vice versa. Further, it is clear that even if the exact eye movement interval is unknown the number of maxima and minima during the light blinking is in the range from n−1 to n+1. In other words it is known where the peaks should be located, i.e. they should be at the same location where the light source flashes. It must of course be understood that the peaks cannot be exactly at that location since due to the human reaction time the patients eyes react slightly behind the light source. This problem is removed by assuming a window around the location of the peak, the length 1 of said window being identical to the illumination time for one light source. Further, it is preferable to locate the center of the window slightly behind the theoretical maximum since it is much more probable that the patient will move his eyes slightly after the light source than before it.

Here it should further be analyzed whether the first window comprises a maximum or a minimum. The signal phase can be investigated by modulating it with a "window signal". This is accomplished by first assuming the coming signal to be a maximum, and setting the windows accordingly. Thereafter the signal sample peak values are multiplied with the value 1 in the maximum windows and with the value −1 in the minimum windows. If the average of the values thus calculated is positive the assumption of the first coming maximum was correct, and if the average becomes negative the first window was set at the location of a minimum.

Thus, the exact positions of the peaks and their maxima $x_p$ are obtained. The next step comprises the exact position of the edges of the triangular area of the peak. The rest noise in the signal makes the definition of the signal's edges using the zero points impossible. Moreover, the last edge of the peak will usually be located farther from the zero point than the first edge.

Here the form of the peak is used as a help. After the median filtering the peak should have straight edges. In FIG. 5 the edges of such a theoretical ideal peak is indicated in phantom line between said maximum $x_p$ and zero points $x_e$. From said figure it is evident that if the average of a local maximum $x_p$ and a point $x_e$ is half of the maximum value said point $x_e$ is a zero point for said peak. In practice, finding the edges and zero points starts from a maximum value and the samples are analyzed one after the other proceeding away from said maximum, until the average of the investigated samples is half the maximum value. A straight line through this point and said maximum point defines the zero point $x_e$ for the peak, which point is needed in the calculations. It should be observed that even if it usually is favorable to calculate said average point for only one of the triangle's sides and thereafter assume the triangle to be an isosceles due to signal symmetry, also the average value for the first edge can be calculated and then the triangle need not necessarily be an isosceles.

Using the maximum points $x_p$ and the zero points $x_e$ obtained in accordance with the above, the area of the triangle peak can easily be calculated. Since the peak represents the derivative for the measured signal the potential leap height can be obtained by integrating over the peak area. This can preferably be done by summing the signal values between said points $x_e$ and then the sum obtained corresponds to the height of one leap. This equation can be expressed as:

$$a = \sum_{i=e}^{S} x_i,$$

where
 a=the leap size
 x=the derivative signal
 s and e are the edges of the peak.

FIG. 6 shows some measured signals (FIGS. 6A, 6B, 6C and 6D) and derivatives (FIGS. 6A', 6B', 6C', and 6D') obtained therefrom using different median filtering lengths 1. As can be seen the obtained derivatives have a very symmetrical form. There is also considerably less rounding of the edges than can be achieved by conventional low pass filtering. It is easier to observe peaks having a regular form and regular edges than it would be in case of a low pass filtered signal. In the example case a median filter length of 1=5 was chosen since it will eliminate most of the noise but hardly distorts the form of the signal at all.

Now there is obtained the size of about 2*30*10 peaks, which will be formed for two eyes during 30 minutes from values taken 10 times a minute. Now a representative for each minute should be calculated from these ten values. FIG. 7 shows as an example the sizes of potential leaps calculated from values for one minute as measured during an actual test series. It is probable that the first value is not reliable. If the measuring series comprise one or more clearly erroneous results like that above, one cannot simply take an average value of the measured series and define it to represent the whole one minute measuring series.

Such error values cannot be eliminated by set threshold values, since the real values vary a lot. One favorable method that has proven to be sufficiently exact is to search for n samples which are as close to each other as possible. The integer n should be sufficiently small in order to eliminate erroneous samples. In tests a value for n corresponding to half the amount of the measured values has proven advantageous. If the number of erroneous values is more than half the amount it is rather impossible with any method to find the real values.

The n specimen of values to be obtained are the points which have the smallest standard deviation and they can be found as follows:

First the average value of the whole set of points is calculated. Thereafter the most remote-point is removed. After this the average value is calculated for the remaining set of points and again the remotest point is removed. This procedure is repeated until there are n points left. Hereafter the average of this set of points represents the whole set of points.

In this manner the number of values needed for the calculation of the coronea-retinal potential is reduced to 2*30 values. In the next step the EOG ratio is calculated from these values. FIG. 8 shows a curve representing such values in a test examination.

Often it is favorable to define the EOG ratio by looking for the curve minimum in the dark interval between 5 and 12 minutes. A minimum found should be checked with respect to its neighbor values in order to ascertain its reliability. A maximum value is obtained in a corresponding manner but from the light test period area. From the maxima and minima obtained the EOG ratio is finally calculated, printed and stored at some preferred means.

Until now an automatic determining of clearly expressable quantities from such signals has proven to be very difficult and unexact. However, the method according to the invention brings about an essential improvement. According to the invention there is now utilized a median filtering, where the signals firstly are suitably digitized in order to exploit all the benefits of the median filtering. Median filtering is namely a very effective way to reduce such random deficiencies which depend on the environment and even on the examined patient's brain functions, which deficiencies in the prior art have constituted a real problem.

The median filtering or calculating the moving average value of the signals is performed by defining a new value for each new point utilizing the average of its neighboring points. This filtering method reduces the noise very efficiently, since the average value for the random noise is zero over the infinite interval. Of course, the interval used in the practical solutions is not infinite, but the filter still attenuates the noise very well. The noise amplitude will roughly be attenuated by a factor 1 (i.e. the length of the filter).

The formula of the median filter is $$y_l = \frac{1}{2l+1} \sum_{n=-l}^{l} x_{i+n} \tag{A}$$

All filters that eliminate noise also destroy some significant information. Also this filter rounds the signal edges, but the length of this rounding is rather short since only the points in near proximity affect the filtered point. This is because the points further than 1 from the point to be filtered cannot have any effect on the result. In this respect a median filter decisively differs from e.g. a low pass filter where all preceding points affect the filtered point.

In order to obtain a signal having clear peaks the signal now must be processed. In a computer this is preferably done in real time so that the number of operations is minimized, and thus the effect simultaneously is maximized. An effective method for reducing the number of operations is often to perform them simultaneously. In this case this is favorably done by combining the median filtering and the differentiating. In the following formulae x is the original signal, y is the median filtered signal and dy is the derivative of the median filtered signal:

$$y_i = \frac{1}{2l+1} \sum_{n=-l}^{l} x_{i+n} \tag{B}$$

$$dy_i = y_i - y_{i-1}$$

When these formulae are combined the following formula is obtained:

$$dy_i = \frac{1}{2l+1} \left( \sum_{n=-l}^{l} x_{i+n} - \sum_{n=-l}^{l} x_{i+n-1} \right) \tag{C}$$

$$dy_i = \frac{1}{2l+1} (x_{i+l} - x_{i-l-1})$$

which for most of the practical embodiments can be reduced to:

$$z_1 = x_{1+l} - x_{i-l-1} \tag{D}$$

The next step in the signal processing is to find the maxima and minima of the derivative signal, and the first problem then is to find local maxima. The task would not be difficult if the signal were completely clean but in the signal in practice there usually are small false maxima, due to the fact that the patient's eye sometimes "gets lost", i.e. it does not actually look directly at the light source 36, 38. However, the correct maxima should be found, and this is performed in the manner described above. When the maxima are found according to the above the edges of the peaks are defined and finally the amplitude size is formed using integration, as above, has been described in greater detail. As the signal in question is a digitized one this can normally be easily performed by summing all signal values between the beginning and end points of a peak value.

Thereafter the EOG ratio must still be calculated on the basis of a set of values consisting of several peak values. In this set there probably still will exist also such values which for some reason do not represent typical values but rather should be considered as errors. For this reason those values which are considered to best correspond to the des-red properties are separated for the calculation. According to a simple solution this elimination is performed using always smaller subsets so that the average of the remaining set is calculated and the farthest value is removed therefrom until suitably about the half of the original values are left. From this subset of values the EOG ratio is now calculated in a manner known per se.

Above a preferred embodiment of the invention has been disclosed, but for the person skilled in the art it is clear that the invention can be varied and adapted in many other ways within the scope of the appended claims.

In addition to the above the enclosed program utilized in the example embodiment is included within this presentation.

20

Source code for the embodiment example program

The EOG measuring program is written in Microsoft C/C++ 7.00 and requires a computer with at least an 80386 CPU and a VGA graphics adapter. It runs under MS-DOS 3.10 or equivalent.

The source code is divided into six different files:

B.1. EOG.H

This file is the header file all modules use. It contains all global function definitions and

```
/* EOG.H - Header file for EOG.C and its modules - VV - 921115 */ void inst_clockd(void);                          /* EOGTIMER.C */
   void deinst_clockd(void);                        /* EOGTIMER.C */
   void onetick(void);                              /* EOG.C */
   void inst_adcard(void);                          /* EOGCARD.C */
   void deinst_adcard(void);                        /* EOGCARD.C */
   void startad(unsigned int);                      /* EOGCARD.C */
   int  getadvalue(void);                           /* EOGCARD.C */
   void setlamp(int);                               /* EOGCARD.C */
   void setled(unsigned int, unsigned int);         /* EOGCARD.C */
   void inst_graph(int);                            /* EOGGRAPH.C */
   void deinst_graph(void);                         /* EOGGRAPH.C */
   void drawcurve(int, int);                        /* EOGGRAPH.C */
   void drawbuffer(void);                           /* EOGGRAPH.C */
   void inst_table(unsigned int, unsigned int,
                   unsigned int, unsigned int,
                   unsigned int);                   /* EOGDATA.C */
   void deinst_table(void);                         /* EOGDATA.C */
   void save(char *);                               /* EOGDATA.C */
   void savevalue(unsigned int, unsigned int,
                  unsigned int, int);               /* EOGDATA.C */
```

B.2. EOG.C

Code that controls other modules. Determines the execution time of different phases of the program (measuring, calculation, etc.). This is the main program itself.

```
/* EOG.C - Electrooculography measuring program
         - Ville Voipio
         - 921108 */

/* Include files */ include <graph.h>
include <malloc.h>
#include <stdio.h>
#include "eog.h"
```

21

```c
/* Definitions */

/* Values of the status byte */ define RECCHNR 0x01          /* Recording channel */
define RECON   0x02          /* Recording on/off */
#define LEDNR   0x04          /* Led nr shining */
#define LEDON   0x08          /* Led on/off */
#define LAMPON  0x10          /* Lamp on/off */
#define END     0x20          /* Measurings done. */

/* Values of the phase flag */ define START 0
define BLINK 1
#define BLINKREC 2
#define WAIT 3

/* Variables */ static unsigned int blinklength, tickcount,
                    samplenr,
                    b_blink, b_blinkrec, b_wait,
                    rounds, darkrounds, roundcount,
                    curphase, blinksleft;

static unsigned gen_status,    /* General flag */
                done;          /* Calculations done? */

/* Initialize variables, etc. */ static void setup(void)
    {
    gen_status = 0;

samplenr = 0;
    roundcount = 0;

blinklength = 150;
    tickcount = blinklength;

darkrounds = 2;
    rounds = 4;

b_blink = 2;
    b_blinkrec = 10;
    b_wait = 10;

curphase = START;
    blinksleft = 0;
    }
```

22

```c
/* Find next thing to do (blink, wait, etc.) */ static void next_phase(void)
   {
   if (curphase == START)
      {
      curphase = BLINK;
      blinksleft = b_blink;
      gen_status |= LEDON;
      return;
      }
   if (curphase == BLINK)
      {
      curphase = BLINKREC;
      blinksleft = b_blinkrec;
      gen_status |= RECON;
      return;
      }
   if (curphase == BLINKREC)
      {
      curphase = WAIT;
      gen_status &= ~(LEDON | RECON);
      setled(0, 0);
      setled(1, 0);

if (roundcount == darkrounds - 1)
         {
         gen_status |= LAMPON;
         blinksleft = b_blink + b_blinkrec + b_wait + b_wait;
         setlamp(1);
         }
      else
         blinksleft = b_wait;

if (roundcount >= rounds - 1)
         gen_status |= END;
      return;
      }
   if (curphase == WAIT)
      {
      curphase = BLINK;
      blinksleft = b_blink;
      gen_status |= LEDON;
      samplenr = 0;
      done = 0;
      roundcount++;
      return;
      }
   }

/* Show one blink */ static void blinkled(void)
   {
   setled(gen_status & LEDNR, gen_status & LAMPON ? 2 : 1);
   setled((gen_status & LEDNR) ^ LEDNR, 0);
   gen_status ^= LEDNR;
   }
```

```
/* One blink */ static void oneblink(void)
   {
   if (!blinksleft)
      next_phase();

if (gen_status & LEDON)
      blinkled();

blinksleft--;
   }

/* One tick */ void onetick(void)
   {
   int sample;

if (gen_status & RECON)              /* To record AD values? */
      {
      sample = getadvalue();
      savevalue(roundcount, samplenr, gen_status & RECCHNR, sample);
      drawcurve(gen_status & RECCHNR, sample);
      if (gen_status & RECCHNR)
         samplenr++;

gen_status ^= RECCHNR;
      startad(gen_status & RECCHNR);
      } tickcount--;
   if (!tickcount)
      {
      oneblink();
      tickcount = blinklength;
      }
   }

/* Main program */ int main(void)
   {
   setup();

inst_adcard();
   printf("A/D-card installed\n");

inst_table(darkrounds, rounds, b_blinkrec * blinklength, b_blinkrec,
              blinklength);
   inst_graph(16);
   inst_clockd();
```

```
                                    24
    while (!(gen_status & END))
       {
       if (kbhit())
          {
          if (getch() == '\x01b')
             break;
          }
       drawbuffer();
       if (curphase == WAIT && !done)
          {
          if (getstepsize(roundcount) == -1)
             break;
          done = 1;
          }
       }
    deinst_clockd();
    deinst_graph();
    save("test.dat");
    deinst_table();
    deinst_adcard();
    }
```

B.3. EOGTIMER.C

Interrupt-related functions. Installs new clock driver and executes original DOS clock interrupts as if there were nothing extra in between hardware and them.

```
/* EOGTIMER.C - PC timer -related functions - VV - 921103 */ include <dos.h>
include "eog.h"

#define TIMER_INTNO 8              /* Timer hardware interrupt */
#define BIOS_DIVISOR 0x10000L      /* Timer division ratio of BIOS */
define DIVISOR_RATIO 16           /* Timer speedup ratio => 291 Hz */ define TIMER_CTR 0x40             /* Timer counter port */
define TIMER_CTL 0x43             /* Timer control port */
define TIMER_MODE 0x36            /* Timer load mode */ define PIC_CMD 0x20               /* Interrupt controller command */
define PIC_EOI 0x20               /* Non-specific end of interrupt */ static void (__interrupt __far * systimer)();
                                   /* Original interrupt */
static int quicktick;              /* Count used for making DOS intr */

/* Set up timer division ratio */ static void settimer(unsigned short ratio)
    {
    _disable();
    _outp(TIMER_CTL, TIMER_MODE);
    _outp(TIMER_CTR, ratio % 0x100);
    _outp(TIMER_CTR, ratio / 0x100);
    _enable();
    }
```

```
/* Substitute clock driver running on faster speed */ static void interrupt far my_inth(void)
    {
    onetick();

quicktick--;
    if (quicktick <= 0)
        {
        _chain_intr(systimer);
        quicktick = DIVISOR_RATIO;
        }

_outp(PIC_CMD, PIC_EOI);
    }

/* Install a new clock driver (my_inth) */ void inst_clockd(void)
    {
    systimer = _dos_getvect(TIMER_INTNO);
    quicktick = DIVISOR_RATIO;

_dos_setvect(TIMER_INTNO, my_inth);
    settimer((unsigned short)((BIOS_DIVISOR / DIVISOR_RATIO) & 0x0000ffffL));
    }

/* Deinstall clock driver */ void deinst_clockd(void)
    {
    settimer((unsigned short)(BIOS_DIVISOR & 0x0000ffffL));
    _dos_setvect(TIMER_INTNO, systimer);
    }
```

B.4. EOGCARD.C

Functions that handle the adapter board. Sampling, LED blinking, lamp control, etc.

```
/* EOGCARD.C - Functions related with commanding AD card - VV - 921103 */ include "eog.h"

/* A/D -card I/O addresses */
#define CARDADD 0x300                       /* Address of the AD card */
define ADCHIP  CARDADD + 0x004             /* Address of the AD chip */ define CH1 0x04                            /* First ECG channel */
define CH2 0x00                            /* Second ECG channel */ define LED1MSK 0x18                        /* xxxLLxxx Led 1 Mask */
define LED2MSK 0x60                        /* xLLxxxxx Led 2 Mask */
#define LED1BRI 0x00                        /* xxx00xxx Led 1 Bright */
#define LED2BRI 0x00                        /* x00xxxxx Led 2 Bright */
#define LED1DIM 0x10                        /* xxx10xxx Led 1 Dim */
#define LED2DIM 0x40                        /* x10xxxxx Led 2 Dim */
#define LED1OFF 0x18                        /* xxx11xxx Led 1 Off */
define LED2OFF 0x60                        /* x11xxxxx Led 2 Off */ define LAMPMSK 0x80                        /* Lxxxxxxx Lamp bit */
define CHMSK   0x07                        /* xxxxxCCC Channel bits */
```

26

```c
/* A general definition (Douglas Adams: Hitchhicker's guide to the galaxy) */
define MOST_UNIVERSAL_NUMBER 42    /* Needs no explanations! */ static unsigned ctlstate;           /* State of the AD card */

/* Send data to the card */ static void setctl(unsigned int mask, unsigned int info)
    {
    info &= mask;
    ctlstate &= ~mask;
    _outp(CARDADD, ctlstate |= info);
    }

/* Initialize the card */ void inst_adcard(void)
    {
    ctlstate = 0;
    setctl(LAMPMSK, 0);
    setctl(LED1MSK, LED1OFF);
    setctl(LED2MSK, LED2OFF);
    setctl(CHMSK, CH1);
    }

/* Start an A/D conversion */ void startad(unsigned int ch)
    {
    setctl(CHMSK, ch ? CH2 : CH1);
    _outp(ADCHIP, MOST_UNIVERSAL_NUMBER);
    }

/* Get one AD reading */ int getadvalue(void)
    {
    unsigned int high, low;

high = _inp(ADCHIP);
    low  = _inp(ADCHIP + 1);

return (((high << 8) + low) >> 4) - 2048;
    }

/* Set the lamp on/off */ void setlamp(int state)
    {
    setctl(LAMPMSK, state ? LAMPMSK : 0);
    }
```

```
/* Set leds on/dim/off */ void setled(unsigned int lednr, unsigned int state)
    {
    if (lednr)
        setctl(LED2MSK, !state ? LED2OFF : (state == 1 ? LED2DIM : LED2BRI));
    else
        setctl(LED1MSK, !state ? LED1OFF : (state == 1 ? LED1DIM : LED1BRI));
    }

/* Reset the card */ void deinst_adcard(void)
    {
    setctl(LAMPMSK, 0);
    setctl(LED1MSK, LED1OFF);
    setctl(LED2MSK, LED2OFF);
    setctl(CHMSK, CH1);
    }
```

B.5. EOGGRAPH.C

Graphics functions. Draws measured data, etc.

```
/* EOGGRAPH.C - Functions related to graphics - VV - 921105 */ include <stdio.h>
include <malloc.h>
#include <graph.h>

/* Definitions related to on-screen graphics */ define VIDEOMODE _VRES16COLOR      /* Video mode to be used */
define SCREENWIDTH 640             /* Pixel width of the screen */
define SCREENHEIGHT 480            /* Pixel height of the screen */ define ZEROCH1 140                 /* y-coordinate of 0 in channel 1 */
define ZEROCH2 340                 /* y-coordinate of 0 in channel 2 */
#define LEFTEDGE 120                /* Left edge of the screen */
#define RIGHTEDGE 520               /* Right edge of the screen */
#define TOPEDGE 40                  /* Upper edge of the screen */
#define CHEDGE 240                  /* Border between channels */
define BOTTOMEDGE 440              /* Bottom edge of the screen */ define CURVE 10                    /* Curve color */
define BORDER 7                    /* Border color */
#define ZEROLINE 9                  /* Zero line color */
define BLANK 0                     /* Background color */ define DBSIZE 8                    /* Size of the display buffer */ struct pix
    {
    int x;
    int y;
    int c;
    };
```

28

```
static int *ptbuffer[2],        /* Saved points */
           xc,                  /* Current x-coordinate */
           scale,               /* y-scale of the signal */
           dbptr;               /* Pointer to dbuffer */
static struct pix dbuffer[DBSIZE]; /* Pixels to be drawn */

/* Initialize graphics */ void inst_graph(int sc)
    {
    int i;

scale = sc;

ptbuffer[0] = (int *)malloc(sizeof(int) * (RIGHTEDGE - LEFTEDGE));
    ptbuffer[1] = (int *)malloc(sizeof(int) * (RIGHTEDGE - LEFTEDGE));
    if (ptbuffer[1] == NULL)
        {
        printf("Not enough memory\a\n");
        exit (-1);
        }
    for (i = 0; i < (RIGHTEDGE - LEFTEDGE); i++)
        {
        ptbuffer[0][i] = -1;
        ptbuffer[1][i] = -1;
        }

_setvideomode(VIDEOMODE);
    _setcolor(BORDER);

_moveto(LEFTEDGE - 1, TOPEDGE - 1);
    _lineto(LEFTEDGE - 1, CHEDGE - 1);
    _lineto(RIGHTEDGE, CHEDGE - 1);
    _lineto(RIGHTEDGE, TOPEDGE - 1);
    _lineto(LEFTEDGE - 1, TOPEDGE - 1);

_moveto(LEFTEDGE - 1, CHEDGE);
    _lineto(LEFTEDGE - 1, BOTTOMEDGE);
    _lineto(RIGHTEDGE, BOTTOMEDGE);
    _lineto(RIGHTEDGE, CHEDGE);
    _lineto(LEFTEDGE - 1, CHEDGE);

_setcolor(ZEROLINE);
    _moveto(LEFTEDGE, ZEROCH1);
    _lineto(RIGHTEDGE - 1, ZEROCH1);

_moveto(LEFTEDGE, ZEROCH2);
    _lineto(RIGHTEDGE - 1, ZEROCH2);

dbptr = 0;
    xc = 0;
    }

/* Save one point to the point buffer */ static void mempixel(int x, int y, int c)
    {
    if (dbptr < DBSIZE - 1)
        {
        dbuffer[dbptr].x = x;
        dbuffer[dbptr].y = y;
        dbuffer[dbptr].c = c;
        dbptr++;
        }
    }
```

```c
/* Draw one point to buffer */ void drawcurve(int ch, int value)
    {
    int y;

ch = ch ? 1 : 0;                    /* Ensure ch = {0, 1} */ y = (ch ? ZEROCH2 : ZEROCH1) - value / scale;

if (!ch)
        {
        if (y < TOPEDGE)
            y = TOPEDGE;
        else if (y >= CHEDGE - 1)
            y = CHEDGE - 2;
        }
    else
        {
        if (y <= CHEDGE)
            y = CHEDGE + 1;
        else if (y >= BOTTOMEDGE)
            y = BOTTOMEDGE - 1;
        } if (ptbuffer[ch][xc] >= 0)
        {
        if (ptbuffer[ch][xc] == (ch ? ZEROCH2 : ZEROCH1))
            mempixel(xc + LEFTEDGE, ptbuffer[ch][xc], ZEROLINE);
        else
            mempixel(xc + LEFTEDGE, ptbuffer[ch][xc], BLANK);
        }
    mempixel(xc + LEFTEDGE, y, CURVE);
    ptbuffer[ch][xc] = y;

if (ch)
        {
        xc++;

if (xc == (RIGHTEDGE - LEFTEDGE))
            xc = 0;
        }
    }

/* Draw points from the buffer */ void drawbuffer(void)
    {
    while (dbptr)
        {
        dbptr--;

_setcolor(dbuffer[dbptr].c);
        _setpixel(dbuffer[dbptr].x, dbuffer[dbptr].y);
        }
    }

/* Deinitialize graphics */ void deinst_graph(void)
    {
    free(ptbuffer[0]);
    free(ptbuffer[1]);
    _setvideomode(_DEFAULTMODE);
    }
```

B.6. EOGDATA.C

All operations that handle the measured data. Finds the leap sizes in the signal.

```c
/* EOGDATA.C - Functions dealing with recorded data - VV - 921108 */ include <stdio.h>
include <malloc.h> define MEDFSIZE 11                    /* Length of the median filter */
define GOODPTS 5                      /* Number of good points */ static int far **samples[2];           /* Info to be saved */
static unsigned int drds, rds, sps,    /* Number of rounds and samples */
                    blinks, blinklength, /* Info needed in eval. step size */
                    mcount, samplesize;

static int *tmptable, *maxt, *mint, *stepsize[2], phasediff;

FILE *tempfile;

/* Allocate data tables */ void inst_table(unsigned int drounds, unsigned int rounds, unsigned int smpls,
                unsigned int blnk, unsigned int blnksize)
   {
   unsigned int i;

samples[0] = (int far **)malloc(rounds * sizeof(int far *));
   samples[1] = (int far **)malloc(rounds * sizeof(int far *));
   for (i = 0; i < rounds; i++)
      {
      samples[0][i] = (int far *)_fmalloc(smpls * sizeof(int));
      samples[1][i] = (int far *)_fmalloc(smpls * sizeof(int));
      if (samples[1][i] == NULL)
         {
         printf("Not enough memory. \a\n");
         exit (-1);
         }
      } stepsize[0] = (int *)malloc(rounds * sizeof(int));
   stepsize[1] = (int *)malloc(rounds * sizeof(int));
   tmptable = (int *)malloc(smpls * sizeof(int));
   maxt = (int *)malloc(blnk * sizeof(int));
   mint = (int *)malloc(blnk * sizeof(int));

if (stepsize[0] == NULL || stepsize[1] == NULL || tmptable == NULL ||
       maxt == NULL || mint == NULL)
      {
      printf("Not enough memory. \a\n");
      exit (-1);
      } drds = drounds;
   rds = rounds;
   sps = smpls;
   blinks = blnk;
   blinklength = blnksize;
   samplesize = sps - MEDFSIZE;
   mcount = blinks;
   phasediff = 3 * blinklength / 16;
   tempfile = fopen("test.log", "w");
   }
```

```
/* Save one data item */ void savevalue(unsigned int round, unsigned int snr, unsigned int channel,
               int value)
   {
   if (round < rds)
      samples[channel ? 1 : 0][round][snr] = value;
   }

/* Save recorded information for further processing */ void save(char *fn)
   {
   int r, s, c, tmp;
   FILE *outfile;

outfile = fopen(fn, "wb");
   if (outfile == NULL)
      {
      printf("Cannot open output file\a");
      exit(-1);
      } fwrite(&sps, 2, 1, outfile);
   fwrite(&drds, 2, 1, outfile);
   tmp = rds - drds;
   fwrite(&tmp, 2, 1, outfile);

for (c = 0; c < 2; c++)
      for (r = 0; r < rds; r++)
         for (s = 0; s < sps; s++)
            {
            tmp = samples[c][r][s];
            fwrite(&tmp, 1, 2, outfile);
            } fclose(outfile);
   fclose(tempfile);
   outfile = fopen("TEST.MAX", "w");
   for (c = 0; c < 2; c++)
      for (r = 0; r < rds; r++)
         fprintf(outfile, "%d\n", stepsize[c][r]);
   fclose(outfile);
   }

/* Calculate derivative of the median of the signal */ static void meddiff(int far *src, int *trg)
   {
   int i;

for (i = 0; i < samplesize; i++)
      trg[i] = src[i + MEDFSIZE] - src[i];
   }
```

32

```c
/* Check if a sample starts with a minimum or a maximum */ static int check_start(void)
    {
    int i;
    long sum;

sum = 0L;

for (i = 0; i < samplesize; i++)
        if (((i + phasediff) / (blinklength / 2)) % 2)
            sum -= tmptable[i];
        else
            sum += tmptable[i];

return (sum < 0L) ? -1 : 1;
    }

/* Take median and difference */ static void med_diff(void)
    {
    int i;

samplesize -= MEDFSIZE;
    for (i = 0; i < samplesize; i++)
        tmptable[i] = tmptable[i] - tmptable[i + MEDFSIZE];
    }

/* Change the sign if necessary */ static long chsign(int side, long l)
    {
    return (side == 1) ? l : -l;
    }
```

33

```
/* Calculate the area of the left side of the peak */ static long leftside(int pos)
   {
   long lim, sum, osum, d1, d2;
   int d1, side;

d1 = tmptable[pos];
   side = (d1 > 0) ? 1 : -1;
   lim = 0L;
   sum = 0L;

do
      {
      sum += 2L * (long)tmptable[pos--];
      lim += (long)d1;
      }
   while (pos && (chsign(side, sum) > chsign(side, lim)));

if (pos == samplesize)
      return sum;

osum = sum - 2L * (long)tmptable[++pos];

d1 = sum - lim;
   d2 = osum - (lim - (long)d1);
   d1 = (d1 < 0) ? -d1 : d1;
   d2 = (d2 < 0) ? -d2 : d2;

if (d1 < d2)
      return sum;
   return osum;
   }

/* Calculate the area of the right side of the peak */ static long rightside(int pos)
   {
   long lim, sum, osum, d1, d2;
   int d1, side;

d1 = tmptable[pos];
   side = (d1 > 0) ? 1 : -1;
   lim = 0L;
   sum = 0L;

do
      {
      sum += 2L * (long)tmptable[pos++];
      lim += (long)d1;
      }
   while ((pos < samplesize) && (chsign(side, sum) > chsign(side, lim)));

if (pos == samplesize)
      return sum;

osum = sum - 2L * (long)tmptable[--pos];

d1 = sum - lim;
   d2 = osum - (lim - (long)d1);
   d1 = (d1 < 0) ? -d1 : d1;
   d2 = (d2 < 0) ? -d2 : d2;

if (d1 < d2)
      return sum;
   return osum;
   }
```

34

```c
/* Calculate area of one peak */ static int peak_area(int pos)
   {
   long area;

area = (leftside(pos) + rightside(pos)) / 2L;
   fprintf(tempfile, "%d\n", area);

return (int)area;
   }

/* Find one minimum */ static int findmin(int pos)
   {
   int cpos, cmin, i, start, end;

fprintf(tempfile, "Min %d ", pos);

start = pos - phasediff;
   if (start < 0)
      start = 0;

end = pos + blinklength / 2 - phasediff;
   if (end > samplesize)
      end = samplesize;

cpos = pos;
   cmin = 0;
   for (i = start; i < end; i++)
      if (tmptable[i] < cmin)
         {
         cpos = i;
         cmin = tmptable[i];
         } fprintf(tempfile, "%d: ", cpos);
   return cpos;
   }
```

35

```c
/* Find one maximum */ static int findmax(int pos)
    {
    int cpos, cmax, i, start, end;

fprintf(tempfile, "Max %d ", pos);

start = pos - phasediff;
    if (start < 0)
       start = 0;

end = pos + blinklength / 2 - phasediff;
    if (end > samplesize)
       end = samplesize;

cpos = pos;
    cmax = 0;
    for (i = start; i < end; i++)
       if (tmptable[i] > cmax)
          {
          cpos = i;
          cmax = tmptable[i];
          } fprintf(tempfile, "%d: ", cpos);
    return cpos;
    }

/* Find the step sizes */ static void getsteps(void)
    {
    int phase, i, b;

phase = check_start();
    for (b = 0, i = 0; b < samplesize; b += blinklength, i++)
       if (phase == 1)
          {
          maxt[i] = peak_area(findmax(b));
          mint[i] = peak_area(findmin(b + blinklength / 2));
          }
       else
          {
          mint[i] = peak_area(findmin(b));
          maxt[i] = peak_area(findmax(b + blinklength / 2));
          }
    }

/* Calculate mean (very mean!) value of table max */ static int aver(void)
    {
    unsigned i;
    long sum;

for (i = 0, sum = 0L; i < mcount; i++)
       sum += maxt[i];

return sum / mcount;
    }
```

36

```c
/* Throw away the worst value */ static void worstout(void)
    {
    unsigned i, wpos;
    int worst, avr;

avr = aver();
    worst = 0;
    wpos = 0;

for (i = 0; i < mcount; i++)
        if (abs(avr - maxt[i]) > worst)
            {
            wpos = i;
            worst = abs(avr - maxt[i]);
            } for (i = wpos + 1; i < mcount; i++)
        maxt[i - 1] = maxt[i];

mcount--;
    }

/* Get the best guess (!!!) of the step size */ static int bestguess(void)
    {
    while (mcount > GOODPTS)
        worstout();

return aver();
    }

/* Find step sizes on different channels and save them */ void getstepsize(unsigned int round)
    {
    printf("Stepsize: %d\r", round);
    meddiff(samples[0][round], tmptable);
    getsteps();
    stepsize[0][round] = bestguess();

meddiff(samples[1][round], tmptable);
    getsteps();
    stepsize[1][round] = bestguess();
    }

/* Free allocated tables */ void deinst_table(void)
    {
    unsigned int r;

for (r = 0; r < rds; r++)
        {
        _ffree(samples[0][r]);
        _ffree(samples[1][r]);
        }
    _ffree(samples[0]);
    _ffree(samples[1]);
    }
```

I claim:

1. A method for performing an electro-oculographic (EOG) examination, wherein alternating optical signals are produced (34, 36) for the stimulation of eye movements and, for the establishment of sample signals, those changes in the bioelectric potential signals are detected (12), which changes are caused by the eye movements corresponding to said optical signals, characterized in filtering (22) noise signals off by forming a moving average from successive sample signal portions, defining from said average signals potential leaps or transitions in the biopotential signals, which transitions are caused by said eye movements, and calculating (24) values corresponding to said transitions, removing possible distorted values from among said values and finally defining the EOG ratio on the basis of values selected from the remaining set of values.

2. A method as defined in claim 1, characterized in converting (18) the bioelectric potential signals to numeric type digital signals prior to the calculation of said moving average.

3. A method as defined in claim 2, characterized in defining from the average signals the local positions of extreme values for the rate of change, preferably by forming windows at the calculated values corresponding to said rate of change in that point which respectively corresponds to said alternation of said optical signals, the window length then preferably corresponding to the time during which each alternating optical signal is on, and defining the quality of the detected extreme value of the rate of change.

4. A method as defined in claim 2, characterized in defining the absolute sizes of said transitions by determining in an area corresponding to said transition the highest individual value (max) for the signal rate of change in a point ($x_p$) and calculating advancing therefrom averages for the rate of change for successive values smaller than said highest individual value up to that point ($x_e$) where said average corresponds to half the said highest individual value, at which point ($x_e$) one of the theoretical zero points is located, the other zero point being defined at a corresponding distance from the location ($x_p$) of said highest value on the opposite side therefrom, and defining the absolute size of said transition as the area of a thus formed triangle ($x_e$, max, $x_e$), suitably as the sum of all individual values located between said defined zero points ($x_e$, $x_e$).

5. A method as defined in any of claim 2, characterized in choosing, for the following calculations, from the set of the absolute values for several transitions the most exact values, suitably about half of all values, by defining continuously smaller partial sets of values, where for each partial set an average is calculated and the value which is farthest away from said average is left out, until the desired amount of values is obtained or the variation is small enough.

6. A method for determining, from a sample signal comprising potential leaps and spurious noise, a reference value for a potential leap, characterized in forming from an analogue sample signal a digital signal succession, from the successive signal portions of which moving averages are calculated, obtaining an approximate potential leap point from said average signals by windowing at an area where a transition is supposed to exist, obtaining in the area of said potential leap the highest individual value for the rate of change, calculating at least one of the theoretical zero points for the change in the potential leap by forming, starting from said highest individual value, the averages of successive values smaller than said highest individual value, a zero point then being defined in the point where, respectively, the calculated average is half of said highest value, and defining a reference value for said potential leaps as the sum of all individual values of the partial set of signals between said zero points.

7. An apparatus for the realization of an EOG examination in accordance with a method disclosed in claim 1, said apparatus comprising means (34, 36) for stimulating the movement of the eyes in a synchronized manner, and means (10) for calculating the EOG rate for the eyes on the basis of detected differences in the biopotential, characterized in that said apparatus comprises means (12) for detecting the differences in biopotential, said differences being caused by the movement of the eyes, means (22) for filtering the top values of signals formed by said biopotential using median filtering, i.e. means for calculating the moving average, as well as means (24) for determining the transitions or potential leaps for said signal top values.

8. An apparatus as defined in claim 7, characterized in that said apparatus comprises means (14) for detecting and amplifying the observed signals, preferably one or more EKG devices or the like, which preferably are such that each comprises three sampler electrodes (12) where said sampler electrodes (12) preferably are so isolated that they have no fixed potential to any potential level.

9. An apparatus as defined in claim 7, characterized in that said apparatus further comprises means (18) for digitizing said signals, said means (18) being connected, with respect to the advancement direction of said signal, before said means (22) arranged for median filtering.

10. An apparatus as defined in any of claim 7, characterized in that said means (22) for accomplishing the median filtering and said means (24) for determining said transitions for said top values comprise mutually integrated means, preferably a computer (20) and soft-ware attached thereto.

11. An apparatus as defined in claim 7, characterized in that said apparatus comprises means (28, 30, 32) for the controlling of means (34, 36, 38) arranged for stimulating the eye's movements, said controlling means (28, 30, 32) functionally being preferably at least partially integral with said means (24) for determining said transition, preferably in connection with said computer (20).

* * * * *